United States Patent [19]

Blanchard et al.

[11] Patent Number: 4,537,894

[45] Date of Patent: Aug. 27, 1985

[54] METHODS OF USING COMPOSITIONS HAVING ANTITHROMBOTIC AND ANTI-BLOOD-PLATELET-AGGREGATING ACTIVITY

[75] Inventors: Jean Blanchard; Edouard Panak, both of Toulouse, France

[73] Assignee: Sanofi, S.A., Paris, France

[21] Appl. No.: 494,133

[22] Filed: May 16, 1983

Related U.S. Application Data

[63] Continuation of Ser. No. 347,700, Feb. 11, 1982, abandoned, which is a continuation of Ser. No. 108,651, Dec. 31, 1979, abandoned, which is a continuation-in-part of Ser. No. 917,374, Jun. 20, 1978, Pat. No. 4,210,649.

[30] Foreign Application Priority Data

Dec. 29, 1978 [GB] United Kingdom ............... 50359/78

[51] Int. Cl.³ .................. A61K 31/415; A61K 31/435
[52] U.S. Cl. .................................... 514/301; 514/302; 514/404; 514/822
[58] Field of Search .................... 424/256, 269, 273 P

[56] References Cited

U.S. PATENT DOCUMENTS 4,075,340  2/1978  Maffrand .............................. 424/256
4,097,482  6/1978  Amselem ........................ 424/256 X

OTHER PUBLICATIONS

Goodman & Gilman–The Pharmacological Basis of Therapeutics, 5th Ed., 1975, pp. 863–864 & 1365–1368.
Packman et al., J. Exp. Med., vol. 126, pp. 171–188 (1967).
Peleirac et al., "Essai Thérapeutique", M.M. No. 205, 12/79, pp. 55–61.

Primary Examiner—Leonard Schenkman
Attorney, Agent, or Firm—Weiser & Stapler

[57] ABSTRACT

This invention relates to a therapeutic composition comprising, as active ingredient, a combination of a pyridine derivative having an anti-blood-platelet-aggregation activity and of sulfinpyrazone.

Said composition has outstanding anti-blood-platelet-aggregating and antithrombotic properties, both components of the active ingredient functioning according to a synergistic effect.

5 Claims, No Drawings

METHODS OF USING COMPOSITIONS HAVING ANTITHROMBOTIC AND ANTI-BLOOD-PLATELET-AGGREGATING ACTIVITY

This application is a continuation of application Ser. No. 06/347,700 filed Feb. 11, 1982, now abandoned which was a continuation of Ser. No. 06/108,651, filed Dec. 31, 1979, now abandoned which was a continuation-in-part of Ser. No. 05/917,374 filed June 20, 1978, now U.S. Pat. No. 4,210,649.

This invention relates to therapeutic compositions having antithrombotic and anti-blood-platelet-aggregation activity comprising, as active ingredients, a combination of a pyridine derivative and 1,2-diphenyl-2'-(phenylsulfinyl-ethyl)pyrazolidine-3,5-dione.

The pyridine derivative is selected from the compounds having the formula:

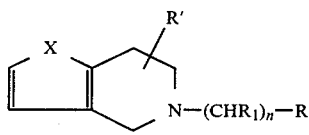

in which:

X represents oxygen or sulfur;

R represents a phenyl or benzoyl group which may carry one or more substituents selected from halogen atoms and the straight- or branched-chain lower alkyl groups, the straight- or branched-chain lower alkoxy groups, the nitro, amino, sulfonylamino, carboxy, lower alkoxycarbonyl, cyano, phenyl, hydroxy(lower)alkyl, methylene-dioxy and ethylene-dioxy groups; an alpha-naphthyl group or a thienyl group;

$R_1$ represents a hydrogen or halogen atom or a hydroxy group, a straight- or branched-chain lower alkyl group, a straight- or branched-chain lower alkoxy group, or a phenyl group;

R' represents a lower alkyl group; and n is an integer from 1 to 15;

and the symbols $R_1$ may have different meanings in each radical $CHR_1$ when n is greater than 1;

and the pharmaceutically acceptable acid addition salts and quaternary ammonium derivatives of said compounds.

The terms "lower alkyl group" and "lower alkoxy group" are intended to mean groups having 1-6 carbon atoms and particularly 1-4 carbon atoms.

Non-limiting Examples of compounds of the formula (I) useful in the therapeutic composition of this invention include:

5-(2-chloro-benzyl)-4,5,6,7-tetrahydro-thieno[3,2-c]pyridine, (ticlopidine);
5-(3,4,5-trimethoxy-benzyl)-4,5,6,7-tetrahydro-thieno[3,2-c]pyridine;
5-(4-methoxy-benzyl)-4,5,6,7-tetrahydro-thieno[3,2-c]pyridine;
5-(2-hydroxy-2-phenyl-ethyl)-4,5,6,7-tetrahydro-thieno[3,2-c]pyridine;
5-p-chlorobenzyl-4,5,6,7-tetrahydro-thieno[3,2-c]pyridine;
5-p-chlorobenzyl-4,5,6,7-tetrahydro-furo[3,2-c]pyridine;
5-(3,5-dimethoxy-benzyl)-4,5,6,7-tetrahydro-thieno[3,2-c]pyridine;
5-(3,4,5-trimethoxy-benzyl)-4,5,6,7-tetrahydro-furo[3,2-c]pyridine;
5-(3-methoxy-benzyl)-4,5,6,7-tetrahydro-thieno[3,2-c]pyridine;
5-(3-methyl-benzyl)-4,5,6,7-tetrahydro-furo[3,2-c]pyridine;
5-(4-methyl-benzyl)-4,5,6,7-tetrahydro-furo[3,2-c]pyridine;
5-(2-fluoro-benzyl)-4,5,6,7-tetrahydro-thieno[3,2-c]pyridine;
5-(3,4-dichloro-benzyl)-4,5,6,7-tetrahydro-thieno[3,2-c]pyridine;
5-(2-phenyl-ethyl)-4,5,6,7-tetrahydro-thieno[3,2-c]pyridine;
5-(2-phenyl-ethyl)-4,5,6,7-tetrahydro-furo[3,2-c]pyridine;
5-(1-methyl-2-hydroxy-2-phenyl-ethyl)-4,5,6,7-tetrahydro-thieno[3,2-c]pyridine;
5-(2-methyl-benzyl)-4,5,6,7-tetrahydro-thieno[3,2-c]pyridine;
5-(3-methyl-benzyl)-4,5,6,7-tetrahydro-thieno[3,2-c]pyridine;
5-(4-methyl-benzyl)-4,5,6,7-tetrahydro-thieno[3,2-c]pyridine;
5-(4-fluoro-benzyl)-4,5,6,7-tetrahydro-thieno[3,2-c]pyridine;
5-(2,6-dichloro-benzyl)-4,5,6,7-tetrahydro-thieno[3,2-c]pyridine;
5-(2-nitro-benzyl)-4,5,6,7-tetrahydro-thieno[3,2-c]pyridine;
5-(4-hydroxy-benzyl)-4,5,6,7-tetrahydro-thieno[3,2-c]pyridine;
5-(2-p-hydroxyphenyl-2-hydroxy-ethyl)-4,5,6,7-tetrahydro-thieno[3,2-c]pyridine;
5-(2-p-methoxyphenyl-2-hydroxy-ethyl)-4,5,6,7-tetrahydro-thieno[3,2-c]pyridine;
5-(2-p-chlorophenyl-2-hydroxy-ethyl)-4,5,6,7-tetrahydro-thieno[3,2-c]pyridine;
5-(2-hydroxy-2-o-methoxyphenyl-ethyl)-4,5,6,7-tetrahydro-thieno[3,2-c]pyridine;
5-(2-hydroxy-2-m-methoxyphenyl-ethyl)-4,5,6,7-tetrahydro-thieno[3,2-c]pyridine;
5-(3-o-chlorophenyl-3-hydroxy-propyl)-4,5,6,7-tetrahydro-thieno[3,2-c]pyridine;
5-(1-phenyl-ethyl)-4,5,6,7-tetrahydro-thieno[3,2-c]pyridine;
5-(3-hydroxy-3-p-nitrophenyl-propyl)-4,5,6,7-tetrahydro-thieno[3,2-c]pyridine;
5-(3-hydroxy-3-phenyl-propyl)-4,5,6,7-tetrahydro-thieno[3,2-c]pyridine;
5-(2-benzoyl-ethyl)-4,5,6,7-tetrahydro-thieno[3,2-c]pyridine;
5-o-bromobenzyl-4,5,6,7-tetrahydro-thieno[3,2-c]pyridine;
5-p-nitrobenzyl-4,5,6,7-tetrahydro-thieno[3,2-c]pyridine;
5-(3-chloro-benzyl)-4,5,6,7-tetrahydro-thieno[3,2-c]pyridine;
5-(3-hydroxy-benzyl)-4,5,6,7-tetrahydro-thieno[3,2-c]pyridine;
5-(2-p-fluoroyphenyl-2-hydroxy-ethyl)-4,5,6,7-tetrahydro-thieno[3,2-c]pyridine;
5-(2,5-dimethoxy-2-phenyl-2-hydroxy-ethyl)-4,5,6,7-tetrahydrothieno[3,2-c]pyridine;
5-(2,3,4-trimethoxy-benzyl)-4,5,6,7-tetrahydro-thieno[3,2-c]pyridine;
5-benzyl-4,5,6,7-tetrahydro-thieno[3,2-c]pyridine;

5-(2-methoxy-benzyl)-4,5,6,7-tetrahydro-thieno[3,2-c]pyridine;
5-(3,4-dimethoxy-benzyl)-4,5,6,7-tetrahydro-thieno[3,2-c]pyridine;
5-[3-(4-fluoro-benzoyl)-propyl]-4,5,6,7-tetrahydro-thieno[3,2-c]pyridine;
5-o-methoxycarbonylbenzyl-4,5,6,7-tetrahydro-thieno[3,2-c]pyridine;
5-o-carboxybenzyl-4,5,6,7-tetrahydro-thieno[3,2-c]pyridine;
5-o-methoxycarbonylbenzyl-6-methyl-4,5,6,7-tetrahydro-thieno[3,2-c]pyridine;
5-(α-naphthyl-methyl)-4,5,6,7-tetrahydro-thieno[3,2-c]pyridine;
5-[(5-chloro-2-thienyl)methyl]-4,5,6,7-tetrahydro-thieno[3,2-c]pyridine;
5-[2-hydroxy-2-(2-thienyl)-ethyl]-4,5,6,7-tetrahydro-thieno[3,2-c]pyridine;
5-o-cyanobenzyl-4,5,6,7-tetrahydro-thieno[3,2-c]pyridine;
5-(3,4-methylenedioxy-benzyl)-4,5,6,7-tetrahydro-thieno[3,2-c]pyridine;
5-[2-(4-bis-phenyl)-2-hydroxy-ethyl]-4,5,6,7-tetrahydro-thieno[3,2-c]pyridine;
5-o-hydroxy-methylbenzyl-4,5,6,7-tetrahydro-thieno[3,2-c]pyridine;
5-benzhydryl-4,5,6,7-tetrahydro-thieno[3,2-c]pyridine;
5-(1-o-chlorophyenyl-butyl)-4,5,6,7-tetrahydro-thieno[3,2-c]pyridine;
5-(1-o-chlorophyenyl-pentyl)-4,5,6,7-tetrahydro-thieno[3,2-c]pyridine;
5-(1-o-chlorophyenyl-propyl)-4,5,6,7-tetrahydro-thieno[3,2-c]pyridine;
5-(1-o-chlorobenzyl-ethyl)-4,5,6,7-tetrahydro-thieno[3,2-c]pyridine;
5-(1-phenyl-ethyl)-4,5,6,7-tetrahydro-thieno[3,2-c]pyridine;

The second component of the composition of this invention, 1,2-diphenyl-(2'-phenylsulfinyl-ethyl)-pyrazolidine-3,5-dione, or sulfinpyrazone, has the following formula:

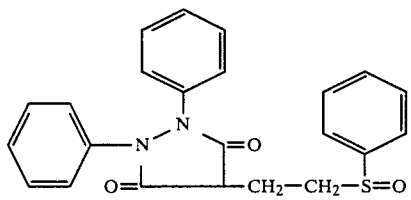

It is described in Merck Index, 9th Edition, 1976, p. 1159. This compound is well known for its anti-gout activity. In addition, it was recently found to have anti-blood-platelet-aggregating properties, as reported in Goodman and Gilman, in *The Pharmacological Basis of Therapeutics*, 5th edition, 1975, which discusses sulfinpyrazone in detail at pages 863-864 and 1365-1368. This entire disclosure is incorporated herein by reference. The discussion on pages 1365-1368 is particularly pertinent since sulfinpyrazone is described as a uricosuric agent which prolongs platelet survival in man. It is also noted there that Packham et al, J. exp. Med. vol. 126, pp. 171-188 (1967) have shown that sulfinpyrazone blocks platelet aggregation in response to collagen and antigen-antibody complexes but not in response to ADP or thrombin.

It has now been found that the combination of a compound of above formula (I) or derivative thereof with sulfinpyrazone produces unexpected effects.

Indeed, the tests effected have shown that the anti-blood-platelet-aggregating and antithrombotic properties of the compounds of the formula (I) were markedly potentiated by the presence of sulfinpyrazone and thus, that the combination possesses anti-blood-platelet-aggregating and antithrombotic activity markedly superior, both qualitatively and quantitatively, to the mere addition of their respective effects.

Such activity is evidenced, for illustrating purposes, using ticlopidine-sulfinpyrazone combination, in the pharmacological investigation reported below together with the toxicological investigation.

I. TOXICOLOGICAL INVESTIGATION

The tests carried out concerned:
(a) the acute toxicity of ticlopidine hydrochloride, of sulfinpyrazone and of the combination of this invention,
(b) their chronic toxicity,
(c) their delayed toxicity,
(d) their local and systemic tolerance, and disclosed that the composition is perfectly tolerated, under the experimental conditions, whether it be by the oral, parenteral or rectal routes, without inducing any local or systemic reaction.

For indicative purposes, the $LD_{50}/24$ hrs/kg body weight, determined with the method according to Miller & Tainter are: in the case of ticlopidine hydrochloride: 1938 mg (p.o.) and 291 mg (i.p.) in rats, 777 mg (p.o.) and 532 mg (i.p.) in mice; and, in the case of sulfinpyrazone 375 mg (p.o.) and 154 mg (iv.) in rats, 298 mg (p.o.) and 240 mg (i.v.) in mice, and 195 mg (i.v.) in rabbits.

It was found from the tests that the toxicity of the combination of this invention is the same as that of its components and that, in that respect, there was no potentation phenomenon.

II. PHARMACOLOGICAL INVESTIGATION

This investigation concerned the anti-blood-platelet-aggregating and antithrombotic activities of the combination of this invention.

(1) Anti-blood-platelet-aggregating action

Blood was taken from the jugular vein of Wistar rats. From this citrated blood, and after centrifugation, was reconstituted a plasma containing 600,000 20,000 blood platelets per $mm^3$ which was used in all aggregation determinations.

(a) Determination of A.D.P. induced blood-platelet aggregation 0.4 ml plasma is placed in a siliconized tube provided with a magnet bar which is also siliconized. The tube is introduced into an aggregometer coupled with an apparatus which records the optical density variations. When light transmission has reached a stable value, 0.5 ml of a solution containing $10\mu$ M A.D.P. (adenosine-di-phosphate) is added to the tube. Blood-platelet-aggregation produces then an increase of light transmission followed by a decrease subsequent to the deaggregation phase.

The maximum optical density variation thus determined characterizes the intensity of the aggregation.

(b) Determination of collagen-induced blood-platelet-aggregation

The A.D.P. solution is substituted with a collagen solution (bovine tendon extract).

(c) Results

Various groups of 20 rats each are used: except for untreated Group I (control), the animals of the other groups are respectively orally administered:

Group 2: 25 mg/kg ticlopidine hydrochloride
Group 3: 50 mg/kg ticlopidine hydrochloride
Group 4: 10 mg/kg sulfinpyrazone
Group 5: 20 mg/kg sulfinpyrazone
Group 6: 25 mg/kg ticlopidine hydrochloride +10 mg/kg sulfinpyrazone
Group 7: 50 mg/kg ticlopidine hydrochloride +20 mg/kg sulfinpyrazone The results of both series of tests, effected with A.D.P. and collagen, are reported in following Table I which indicates the percent inhibition of blood-platelet aggregation obtained, with respect to the control group, 3 hours after treatment with the test compound.

TABLE I

| Treatment | Percent Inhibition | |
|---|---|---|
| | A.D.P. | Collagen |
| Group 2 | 28.5 | 48.6 |
| Group 3 | 40.6 | 58.3 |
| Group 4 | 8.7 | 12.7 |
| Group 5 | 14.1 | 20.5 |
| Group 6 | 50.8 | 78.2 |
| Group 7 | 64.9 | 96.8 |

(2) Anti-thrombotic action

This investigation concerned myocardial necrosis induced in animals under severe stress conditions which may be reproduced by infusion of adrenalin.

Mongrel dogs of either sex, weighing about 10 kg, were distributed into groups of 5 animals each: except for one group of untreated dogs (controls, Group 1), the other groups were orally administered the test material, twice a day, for 4 days, repsectively:

Group 2: 50 mg/kg ticlopidine hydrochloride
Group 3: 100 mg/kg ticlopidine hydrochloride
Group 4: 20 mg/kg sulfinpyrazone
Group 5: 40 mg/kg sulfinpyrazone
Group 6: 50 mg/kg ticlopidine hydrochloride +20 mg/kg sulfinpyrazone
Group 7: 100 mg/kg ticlopidine hydrochloride +40 mg/kg sulfinpyrazone Eighteen hours after the last treatment the dogs were anesthetized with phenobarbital (25 mg/kg, i.v.); a catheter was placed in the femoral artery, the blood pressure was recorded via a STAHAM P 23 GD sensor and the ECG was recorded ($D_1$ and $D_2$) with a RACIA polygraph. The adrenalin was infused by the cephalic route at a dosage of 4 μg/kg/mn at a rate of 2 ml/mn for 4 hours.

Arterial blood samples were taken before and after the end of the infusion, to effect the blood-platelet counts.

The animals were freed from the catheters and were allowed to wake up. The animals which survived 7 days later were sacrificed and autopsied; the hearts were cut out and examined macroscopically prior to taking samples for histological examination. Any macroscopic anomalies are rated according to the following code (Table II) which was established arbitrarily and which takes into account the extent of the damages (p.9).

The following results were obtained:

Blood-platelet count:

The blood-platelet count effected immediately prior to and after adrenalin infusion shows a 32.4% decrease in the controls (Group I). In contrast, in the treated animals, the count tends to increase, with the exception, however, of those which were administered only sulfinpyrazone.

Group 2: +14%
Group 3: +13.2%
Group 4: −12%
Group 5: −7%
Group 6: +18.5%
Group 7: +19.4%

Survival Time:

The number of animals that survived on the 7th day after adrenalin infusion is reported below:

Group 1: 2/5
Group 2: 3/5
Group 3: 4/5
Group 4: 2/5
Group 5: 2/5
Group 6: 4/5
Group 7: 5/5

Macroscopic Lesions:

It is found that the treated animals reach necrosis scores (calculated according to the above Table) of a markedly lesser magnitude than the controls; the necrosis scores of the animals administered only sulfinpyrazone are substantially identical with those of the controls:

Group 1: (control: 18.0
Group 2: 6.8
Group 3: 4.8
Group 4: 18.2
Group 5: 17.4
Group 6: 1.6
Group 7: 1.1

TABLE II

| Parts observed | Extent of the Involvement | Entirely hemorragic | Large hemorragic areas | Numerous hemorragic points | Some hemorragic points | Small hemorragic or necrotic point |
|---|---|---|---|---|---|---|
| Exterior | Percardium | 5 | 4 | 3 | 2 | 1 |
| | Left ventricle | 5 | 4 | 3 | 2 | 1 |
| | Right ventricle | 5 | 4 | 3 | 2 | 1 |
| | Left auricle | 5 | 4 | 3 | 2 | 1 |
| | Right auricle | 5 | 4 | 3 | 2 | 1 |
| Cavities | Left ventricle | 5 | 4 | 3 | 2 | 1 |
| | Right ventricle | 5 | 4 | 3 | 2 | 1 |
| | Left auricle | 5 | 4 | 3 | 2 | 1 |
| | Right auricle | 5 | 4 | 3 | 2 | 1 |

It may be concluded, from the set of results obtained, that intravenous perfusion of adrenalin induces in the controls serious disorders which are essentially shown by a drop of the number of blood-platelets and by a myocardial involvement of necrotic type. In contrast, pretreatment with ticlopidine hydrochloride provides significant protection against myocardia necrosis, improves the survival time and increases the number of blood-platelets. Said results are enhanced when ticlopidine hydrochloride is combined with sulfinpyrazone, both compounds thus functioning according to a synergistic effect. It should be noted that sulfinpyrazone, when administered individually, has no effect on the blood-platelet count, on the survival time and on the macroscopic lesions.

The toxicological and pharmacological investigations reported above show the usefulness of the combination of this invention. Indeed, while it possesses an excellent tolerance and a low toxicity, this combination produces also a marked enhancement of the blood-platelet aggregation inhibiting and antithrombotic properties of the derivatives of formula (I) due to the presence of sulfinpyrazone.

In view of this outstanding potentation action, the combination of this invention may be usefully administered for human and veterinary therapeutic purposes.

The active ingredients are generally used together with a therapeutically administrable carrier. Thus, the composition of this invention may advantageously be formulated as tablets, coated tablets or capsules for oral administration, and as suppositories for rectal administration.

Each unit dose will advantageously contain 0.05–0.200 g of a compound or derivative of the formula (I) and 0.010–0.150 g of sulfinpyrazone. The daily dosage regimen may vary from 0.05 g to 1 g for the compounds or derivatives of formula (I) and from 0.010 g to 0.600 g for sulfinpyrazone.

Non-limiting Examples of pharmaceutical formulations of the compositions of this invention are given below:

1. Tablets
   Ticlopidine hydrochloride 0.150 g
   Sulfinpyrazone 0.075 g
   Excipients: polyvinylpyrrolidone, corn starch, magnesium stearate, talc.
2. Coated Tablets
   Ticlopidine hydrochloride 0.200 g
   Sulfinpyrazone 0.100 g
   Excipients: magnesium stearate, calcium carbonate, talc, gum arabic, shellac, rosin, glucose, sucrose, white wax.
3. Capsules
   Ticlopidine hydrochloride 0.100 g
   Sulfinpyrazone 0.100 g
   Excipients: lactose, stearic acid, magnesium stearate In view of its blood-platelet-aggregation inhibiting and antithrombotic properties, the compositions of this invention are applicable for the prevention and treatment of diseases inducing a pathological change in blood-platelet aggregation, such as the thromboembolic diseases.

While the invention has been described herein with particular reference to the preferred combination of active ingredients, i.e., sulfinpyrazone and ticlopidine hydrochloride, and to methods and dosage units for the oral and rectal administration thereof, it will be apparent to those skilled in the art that this disclosure is equally applicable to all of the other combinations of active ingredients disclosed herein. The excipients, formulations and method of administration will be the same in all cases, although the various combinations of ingredients will, of course, vary in potency or effect, and, therefore, the dosage levels may be varied accordingly.

What is claimed is:

1. A method for the prevention or treatment of a disease inducing pathological change in blood-platelet-aggregation in a patient subject to or suffering from such a disease, comprising administering to said patient in an amount effective for prevention or treatment of said disease, sulfinpyrazone and a pyridine derivative, for causing antithrombotic and anti-blood-platelet-aggregation activity, the blood platelet aggregation being A.D.P. induced, said pyridine derivative being selected from the group consisting of compounds having the formula:

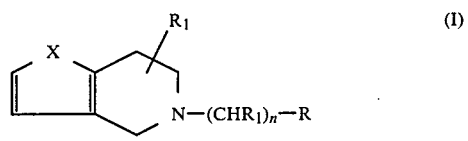

in which
X represents oxygen or sulfur;
R is selected from the group consisting of unsubstituted phenyl and benzoyl, phenyl and benzoyl having at least one substituent selected from the group consisting of halogen, straight or branched-chain lower alkyl, straight- or branched-chain lower alkoxy, nitro, amino, sulfonylamino, carboxy, lower alkoxycarbonyl, cyano, phenyl, hydroxy alkyl, methylene-dioxy and ethylene-dioxy, and an alpha-naphthyl group or a thienyl group;
$R_1$ represents a hydrogen or halogen atom or a hydroxy group, a straight- or branched-chain lower alkyl group, a straight- or branched-chain lower alkoxy group, or a phenyl group;
R' represents a lower alkyl group; and
n is an integer from 1 to 15; and the symbols $R_1$ may have different meanings in each radical $CHR_1$ when n is greater than 1;
and the pharmaceutically acceptable acid addition salts and quaternary ammonium derivatives of said compounds.

2. The method of claim 1 wherein the pyridine derivative is 5-(2-chloro-benzyl)-4,5,6,7-tetrahydrothieno(3,2-c)pyridine, (ticlopidine)hydrochloride.

3. The method of claim 1 wherein the composition is administered in a daily dosage of from about 0.01 to about 0.6 g of sulfinpyrazone and about 0.5 to about 1 g of the pyridine derivative.

4. The method of claim 3 wherein the composition is administered orally.

5. The method of claim 1 wherein said pyridine derivative is selected from the group consisting of 5-(2-chlorobenzyl)-4,5,6,7-tetrahydrothieno[3,2-c]pyridine, (ticlopidine) and the pharmaceutically acceptable acid salts and quaternary ammonium derivatives thereof and wherein sulfinpyrazone is present in said composition in an amount effective to enhance the antithrombotic property of said pyridine derivative.

* * * * *